(12) United States Patent
Qi

(10) Patent No.: US 12,247,207 B2
(45) Date of Patent: Mar. 11, 2025

(54) LONG-CHAIN NON-CODING RNA BASED BCL2 GENE INHIBITOR

(71) Applicant: SOOCHOW UNIVERSITY, Suzhou (CN)

(72) Inventor: Xiaofei Qi, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 1220 days.

(21) Appl. No.: 17/003,925

(22) Filed: Aug. 26, 2020

(65) Prior Publication Data

US 2020/0392514 A1 Dec. 17, 2020

Related U.S. Application Data

(63) Continuation of application No. PCT/CN2018/077463, filed on Feb. 27, 2018.

(51) Int. Cl.
*C12N 15/64* (2006.01)
*A61K 31/7105* (2006.01)
*A61K 45/06* (2006.01)

(52) U.S. Cl.
CPC .......... *C12N 15/64* (2013.01); *A61K 31/7105* (2013.01); *A61K 45/06* (2013.01); *C12N 2310/11* (2013.01)

(58) Field of Classification Search
CPC .......................... A61K 31/7105; A61K 45/06
See application file for complete search history.

(56) References Cited

FOREIGN PATENT DOCUMENTS

WO    2008144506 A1    11/2008

OTHER PUBLICATIONS

Qi et al, "H22954, a novel long non-coding RNA down-regulated in AML, inhibits cancer growth in a BCL-2-dependent mechanism", Cancer Lett. Jul. 10, 2019;454:26-36 (Year: 2019).*
Genbank Accession No. AF363578., GenBank Database, Dec. 2, 2008.
Chen, Jiahui et al., "The long noncoding RNA ASNr regulates degradation of Bcl-2 mRNA through its interaction with AUF1," Scientific Reports, Aug. 31, 2016.

* cited by examiner

*Primary Examiner* — Amy E Juedes
*Assistant Examiner* — Peter Johansen
(74) *Attorney, Agent, or Firm* — SZDC Law PC

(57) ABSTRACT

The present invention identified BCL2 gene inhibitor based on long non-coding RNA, the sequence of SEQ ID NO: 1; Which could interact with BCL2 and inhibit its expression effectively, thereby inhibiting the growth and metastasis of tumor, and benefiting patients in the process of tumor treatment.

1 Claim, 3 Drawing Sheets

Specification includes a Sequence Listing.

LONG-CHAIN NON-CODING RNA BASED BCL2 GENE INHIBITOR

This application is a Continuation Application of PCT/CN2018/077463, filed on Feb. 27, 2018, which is which is incorporated by reference for all purposes as if fully set forth herein.

TECHNICAL FIELD

The present invention relates to the gene therapy technology, and more specifically, a BCL2 gene inhibitor based on long non-coding RNA.

BACKGROUND TECHNIQUE

BCL2 was a gene that inhibits apoptosis. Abnormal expression in malignant cells of tumors such as acute myeloid leukemia and acute lymphoid leukemia, so that these tumor cells can gain growth advantages and fight against the body's defense system and some anticancer drugs. A growing number of studies have reported that inhibition of BCL2 gene expression can inhibit tumor growth and metastasis, benefiting patients in the treatment of tumors; conversely, drugs that inhibit tumors are almost ineffective against BCL2 gene suppression. Therefore, it was necessary to develop new drugs to inhibit the expression of the BC L2 gene.

SUMMARY OF INVENTION

The invention discloses a new BCL2 gene expression inhibitor, which can inhibit its expression effectively, thereby inhibiting the growth and metastasis of tumor, and benefiting patients in the process of tumor treatment.

This invention adopts the technical solution is as follows:

Application of long non-coding RNA in synthesis of the BCL2 gene inhibitor; the sequence of the long non-coding RNA was SEQ ID NO: 1.

Application of long non-coding RNA for inhibiting the BCL2 gene; the sequence of the long non-coding RNA was SEQ ID NO: 1.

A kind of BCL2 gene inhibitor, which is a long non-coding RNA, and the sequence of the long non-coding RNA was SEQ ID NO: 1.

A method of preparation for the antineoplastic includes that a long non-coding RNA was transferred into the plasmid vector to obtain the antineoplastic; and the sequence of the long non-coding RNA was SEQ ID NO: 1.

In the present invention, the sequence of SEQ ID NO: 1 is as follows:

```
GGTGATGGGAAATTTCAGACTTTGATTTGGGCCTTGGAAAACAGGTTCAG

TTTCAGTAGATGGAGGTAAAAGGAGGCAAAGAGCGACCTTACGTAAATCC

AAGGCTGAAGGAAGGAGGCTCTAAGGGGTGTGTGGGTGATTAGGAGTAAA

GTATCTTGTCTGAAATGAAGAGTTTCTATACAGCATGCTTATTTGGAGTC

ATGCCTAACAAGATTACTTTGGGTCTAATTTTGGAAGCTTGGTACTCCAG

GGAGCTTGGACATGAATTTAAAGACAATGGGAACTCACATTTAAGTTTCT

GAAACAGCCAGGCGTGGTGGCTCATGCCTGTAATCCCAGCACTTCGGGAG

GCTGAGGCAGGTGGATCACCTGAGATCAGGAGTTTGAGACCAGTCTAACC

AACATGGAGAAACCCCATCTCTACTTAAAAG.
```

Advantageous Effects of the Invention

The present invention discloses a novel long non-coding RNA that is able to inhibit BCL2 gene expression, with the sequence of SEQ ID NO: 1; the long non-coding RNA could interact with BCL2 and inhibit its expression effectively, thereby inhibiting the growth and metastasis of tumor, and benefiting patients in the process of tumor treatment.

INVENTION EMBODIMENT

Example 1

The present invention discloses a long non-coding RNA (called H22954) that is able to inhibit BCL2 gene expression, the sequence of SEQ ID NO: 1 is as follows:

```
GGTGATGGGAAATTTCAGACTTTGATTTGGGCCTTGGAAAACAGGTTCAG

TTTCAGTAGATGGAGGTAAAAGGAGGCAAAGAGCGACCTTACGTAAATCC

AAGGCTGAAGGAAGGAGGCTCTAAGGGGTGTGTGGGTGATTAGGAGTAAA

GTATCTTGTCTGAAATGAAGAGTTTCTATACAGCATGCTTATTTGGAGTC

ATGCCTAACAAGATTACTTTGGGTCTAATTTTGGAAGCTTGGTACTCCAG

GGAGCTTGGACATGAATTTAAAGACAATGGGAACTCACATTTAAGTTTCT

GAAACAGCCAGGCGTGGTGGCTCATGCCTGTAATCCCAGCACTTCGGGAG

GCTGAGGCAGGTGGATCACCTGAGATCAGGAGTTTGAGACCAGTCTAACC

AACATGGAGAAACCCCATCTCTACTTAAAAG.
```

Example 2

Cell transfection and western blotting. Transfected into K562 cells with long non-coding RNA (SEQ ID NO:1) by Lipofectamine 2000 (Invitrogen). The cells were cultured for 24-48 hours and mixed with 50 mmol/L Tris-HCl (pH8.0), 150 mmol/L NaCl, 1% (v/v) Triton X-100 and protease inhibitor mixture (1:100 diluted, Sigma). To analysis of protein by SDS-PAGE and western blot. The film was developed and exposed to X-ray film with ECL reagent (Denville scientific).

Figure 1:
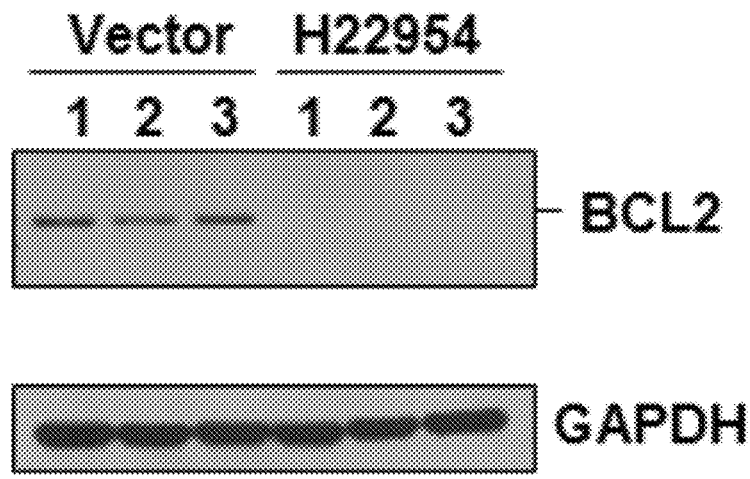
FIG. 1 shows the expression of BCL2 protein in K562 cells with stable and high expression of h22954.

The cultured stable leukemia cell line K562 expressing H22954 was analyzed by protein electrophoresis after lysis, and BCL2 was significantly decreased compared with non-high-cell cells, see FIG. 1. 1, 2, 3 are empty vectors (Vector) for 3 stable strain controls, 4, 5,6 .

The 3 strains of K562 expressed stably H22954. GAPDH is the loading control. Under the condition of similar expression of GAPDH, the expression level of BCL2 was significantly lower in the stable strain with high expression of H22954 than in the empty vector control group.

Figure 2:
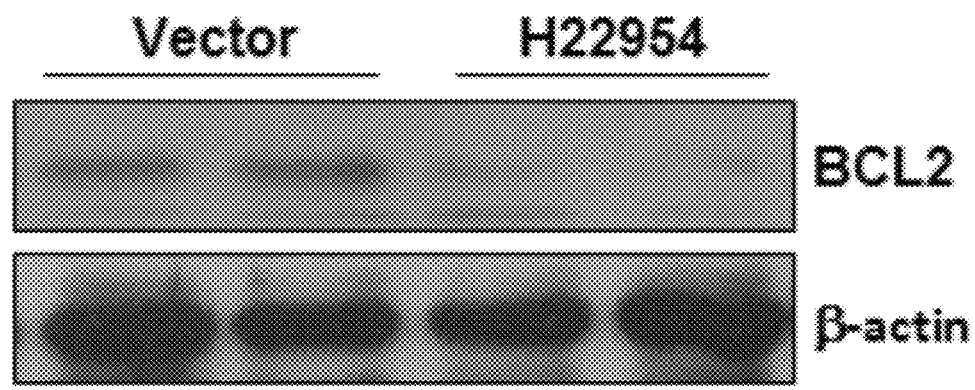
FIG. 2 shows the expression of BCL2 protein in transplanted tumor of mouse K562 cells.

In the mouse model of subcutaneous xenograft, the transplanted tumor with high expression of H22954, BCL2 decreased, see FIG. 2.

Vector was empty body group. H22954 is a transplanted tumor formed by a K562 stable strain highly expressing H22954. GAPDH is the loading control. Under the condition of similar expression of GAPDH, the expression of BCL2 in the transplanted tumor formed by the stable strain with high expression of H22954 was significantly lower than that of the empty vector control group.

Example 3

Determination of luciferase. 293 cells were transfected with and long non-coding RNA (SEQ ID NO:1) expression plasmid or control vector (empty vector PGL3 and gene with no interaction with H22954 PGL3-Contr01) and 1 μg of luciferase reporter gene vector together with Lipofectamine 2000 reagent (Invitrogen). To normalize the efficiency of transfection in each transfection, 50 ng of the pRLTK plasmid (Promega) was used in each well. Luciferase activity was measured by the dual luciferase reporter assay system (Promega).

Figure 3:
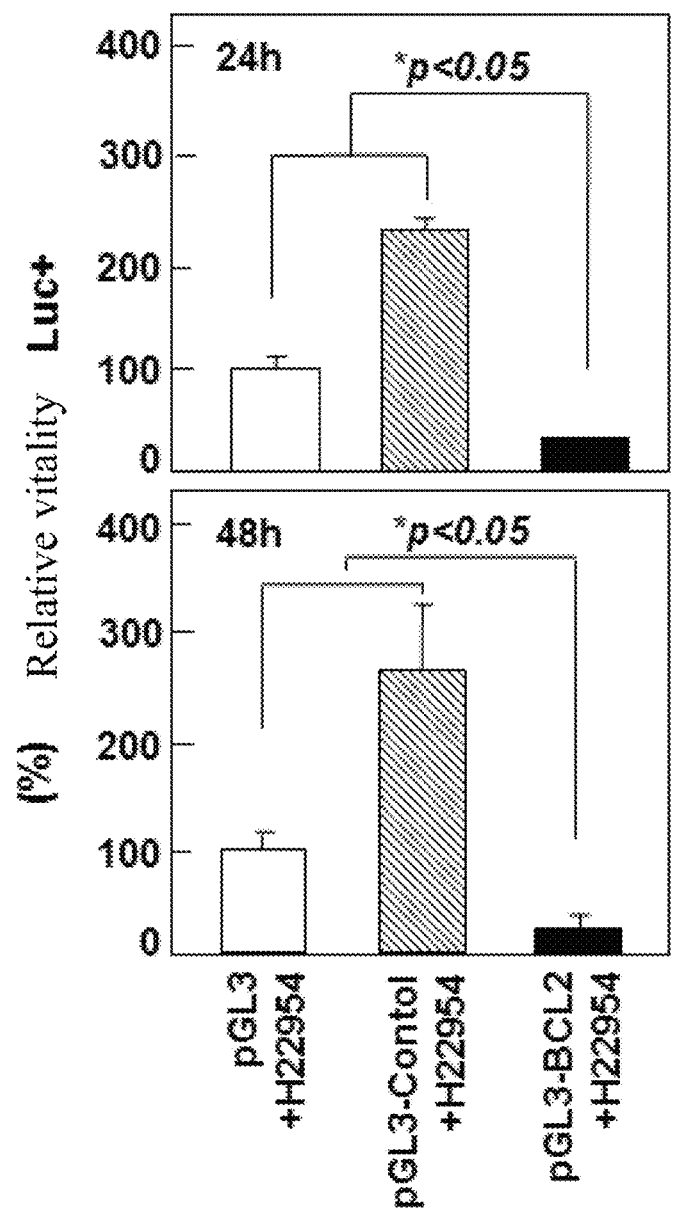
FIG. 3 shows the determination of luciferase reporter gene.

Carried a long non-coding RNA (SEQ ID NO: 1) plasmid or a control empty vector plasmid was transferred into 293 cells by liposome and simultaneously transferred into a fluorescein reporter plasmid carrying BCL2, 24-48 hours later, Fluorescence intensity was observed, and the long non-coding RNA (SEQ ID NO: 1) was significantly attenuated in the plasmid group, see FIG. 3. 293 cells were transfected and long non-coding RNA (SEQ ID NO: 1) expression plasmid or control vector (empty vector PGL3 and gene with no interaction with H22954 PGL3-Control) and 1 μg of luciferase reporter gene vector together with Lipofectamine 2000 reagent (Invitrogen). After 24-48 hours, the fluorescence intensity was observed. Compared with the empty vector and H22954 non-interacting gene, the fluorescence of the long non-coding RNA (SE Q ID NO: 1) plasmid group was significantly attenuated.

Example 4

Admeasurement of RNA antisense purification (RAP). Briefly, heat-denatured biotinylated DNA oligonucleotide probes complementary to target RNA (SEQ ID NO: 1) and 5'-biotin were pre-treated with GuSCN hybridization buffer (20 mM Tris-HCl). (pH 7.5), 7 mM EDTA, 3 mM EGTA, 150 mM LiCl, 1% NP-40, 0.2% N-lauroyl sarcosine, 0.1% sodium deoxycylate, 3M guanidinium thiocyanate and 2.5 mM TCEP) Incubate for 2 hours at 37° C. with intermittent shaking, pre-washed streptavidin magnetic beads were added and incubated at 37° C. for 30 minutes, then shaken and washed. Magnetic beads were magnetically separated and washed with RNase H elution buffer (50 mM Tris-HCl (pH 7.5), 75 mM NaCl, 3 mM $MgCl_2$, 0.125% N-lauroyl sarcosine, 0.025% sodium deoxycholate and 2.5 mM TCEP) Tu. The RNA complex was eluted and subjected to qPCR assay (95° 10 min, 40 cycles, 95°30", 60°1') to quantify RNA yield and enrichment.

Figure 4:
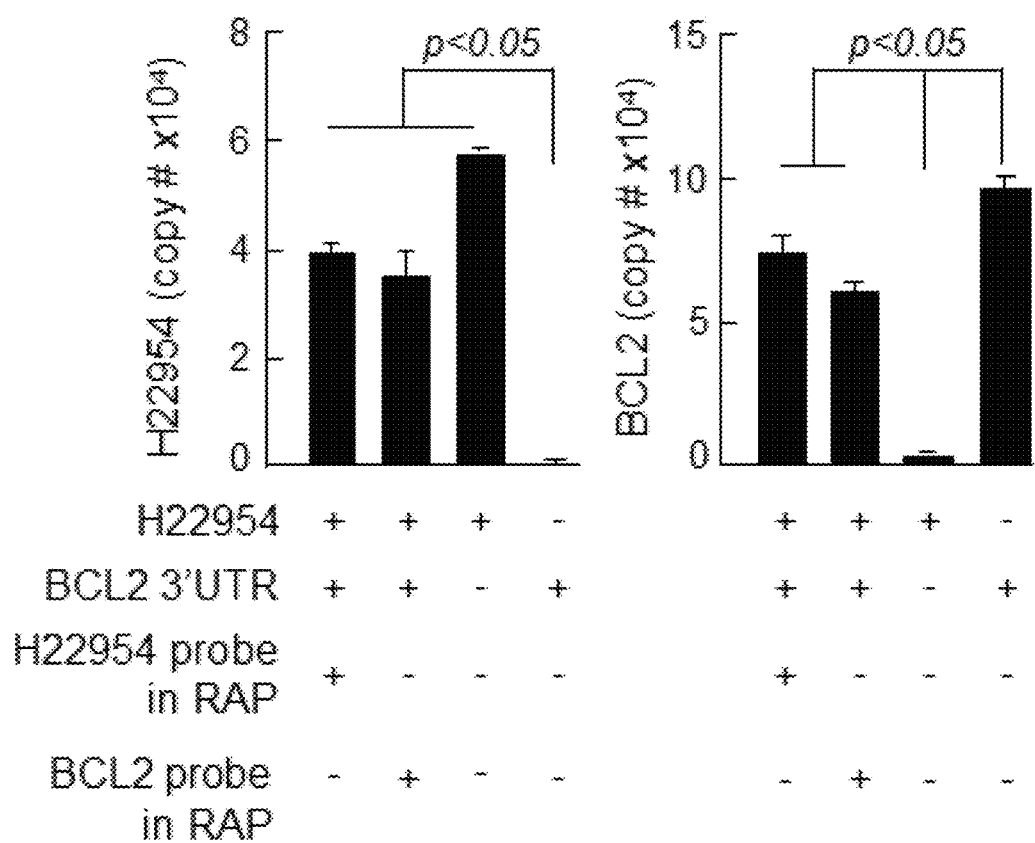
FIG. 4 shows the measurement of RNA antisense purification (RAP).

Long non-coding RNA (SEQ ID NO: 1) fragment, BCL2 fragment were added to the hybridization solution, and biotin-labeled probe was added. After reacting for 37 hours at 37 degrees, streptomycin-labeled magnetic beads were added, 37 degrees 30 Minutes, put in magnetic field sorting, wash and then qPCR (95° 10 minutes, 40 cycles, 95°30", 60°1). It can be seen that the probe of H22954 can bind to BCL2 while binding to H22954. The probe of BCL2 can also bind to H22954, see FIG. 4. The left picture shows the results of quantitative PCR of H22954. The first column was the positive control of the reaction system, and the 3'UTR fragment of H22954 and BCL2 was added to the reaction system. A probe capable of binding to H229 54 was added. Quantitative PCR was performed after purification. The second column was an experimental group, and a 3'UTR fragment of H22954 and BC L2 was added to the reaction system, and then a probe capable of binding to BCL2 was added. The third four column was the PCR system control, and the corresponding fragment was directly added to the final eluate for quantitative PCR. The right picture shows the results of H22954 quantitative PCR, wherein the first column was the experimental group, and the reaction system was added with H22954 and BC After the 3'UTR fragment of L2, a probe capable of binding to H22954 was added. Quantitative PCR was performed after purification. The second column was a positive control of the reaction system, and the 3'UTR fragment of H22954 and BCL2 was added to the reaction system, and then added to bind. The probe of BCL2 was purified and quantified by PCR. The third four column was the PCR system control, and the corresponding fragment was directly added to the final eluate for quantitative PCR. As a result, the H22954 probe can purify BCL2 while purifying itself. The BCL2 probe can also purify the H22954 fragment. It was indicated that H22954 and BCL2 can bind to each other.

The invention claimed is:

1. A method of preparing an antineoplastic composition comprising:
    transferring an isolated non-coding DNA consisting of a nucleotide sequence of SEQ ID NO: 1 into a plasmid vector; and
    obtaining the antineoplastic composition containing the plasmid vector.

* * * * *

SEQUENCE LISTING

```
<160> NUMBER OF SEQ ID NOS: 1

<210> SEQ ID NO 1
<211> LENGTH: 431
<212> TYPE: DNA
<213> ORGANISM: Artificial sequence
<220> FEATURE:
<223> OTHER INFORMATION: Non-coding RNA

<400> SEQUENCE: 1
ggtgatggga aatttcagac tttgatttgg gccttggaaa acaggttcag tttcagtaga      60
tggaggtaaa aggaggcaaa gagcgacctt acgtaaatcc aaggctgaag gaaggaggct     120
ctaaggggtg tgtgggtgat taggagtaaa gtatcttgtc tgaaatgaag agtttctata    180
```

```
cagcatgctt atttggagtc atgcctaaca agattacttt gggtctaatt ttggaagctt    240
ggtactccag ggagcttgga catgaattta aagacaatgg gaactcacat ttaagtttct    300
gaaacagcca ggcgtggtgg ctcatgcctg taatcccagc acttcgggag gctgaggcag    360
gtggatcacc tgagatcagg agtttgagac cagtctaacc aacatggaga aaccccatct    420
ctacttaaaa g                                                        431
```